United States Patent [19]
Nozaki

[11] Patent Number: 4,973,827
[45] Date of Patent: Nov. 27, 1990

[54] DISINFECTOR UNITS FOR CONTACT LENSES

[75] Inventor: Zenkichi Nozaki, Ageo, Japan

[73] Assignee: Asahi Irika Co., Ltd., Saitama, Japan

[21] Appl. No.: 414,365

[22] Filed: Sep. 29, 1989

[30] Foreign Application Priority Data

Oct. 26, 1988 [JP] Japan .................... 63-269840

[51] Int. Cl.$^5$ .................................... H01R 29/00
[52] U.S. Cl. .................................... 219/521; 439/173; 219/386
[58] Field of Search ............... 219/521, 385, 386, 387; 439/166, 170, 171, 173, 174, 175

[56] References Cited

U.S. PATENT DOCUMENTS

| | | | |
|---|---|---|---|
| 2,277,605 | 3/1942 | Palitzsch | 219/521 |
| 2,450,657 | 10/1948 | Guernsey | 439/173 |
| 3,343,056 | 9/1967 | Hirschmann | 439/173 |
| 4,044,226 | 8/1977 | Kadlecik et al. | 219/521 |
| 4,072,091 | 2/1978 | Richardson | 219/521 |
| 4,158,126 | 6/1979 | Seitz | 219/439 |
| 4,178,499 | 12/1979 | Bowen | 219/439 |
| 4,235,842 | 11/1980 | Thomas et al. | 422/116 |
| 4,677,280 | 6/1987 | Kai | 219/385 |
| 4,701,597 | 10/1987 | Braun | 219/386 |
| 4,856,999 | 8/1989 | Flohr | 439/171 |

FOREIGN PATENT DOCUMENTS 0104279 4/1984 European Pat. Off. ........... 439/175
61-244362 4/1985 Japan.

Primary Examiner—Teresa J. Walberg
Attorney, Agent, or Firm—Christopher John Rudy

[57] ABSTRACT

A disinfector unit for contact lenses making use of a commercial power source, which can be used corresponding to commercial power source outlets of standards varying with countries and districts, i.e., various types of outlets operable at varying voltages, includes a heater element for receiving a power of varying voltages to heat a contact lens held in a lens case placed in a lens case holder to a predetermined temperature, an electrical controller therefor and a plurality of plugs, each including a case body provided in its one side with a cavity and an electric conductor from which varying types of inserts extend. The plug having the inserts coinciding with an outlet of commercial power used is selected and fitted in the cavity in the case body, and the extending inserts are plugged into the outlet to supply current for predetermined disinfection.

5 Claims, 4 Drawing Sheets

4,973,827

DISINFECTOR UNITS FOR CONTACT LENSES

BACKGROUND OF THE INVENTION

1. Field of the Invention

The present invention relates to a disinfector unit which is used for disinfecting bacterial microorganisms sticking to contact lenses by boiling, and designed to use commercial power as a power source and, more particularly, to a disinfector unit which is usable in various countries where varying voltages and varying types of outlets are prescribed to be applied.

2. Prior Art

Because of their liability to bacterial deposition, soft types of contact lenses are disinfected in a liquid preservative by boiling for each wearing, and this is generally achieved with disinfector units making use of commercial power for domestic purposes, since daily care is needed under such conditions as defined in terms of a temperature of 80° C. and a time length of 10 minutes or longer (see, e.g., U.S. Pat. Nos. 4,044,266, 4,158,126, 4,178,499 and 4,235,842).

Other disinfector units known in the art are miniaturized by the application of PTC heater elements or integrated circuits (or ICs for short) and designed to dispense with any cord and include a plug in a case as an integral piece for making easy storage and handling such as in carrying in travels (see Japanese Patent Laid-Open No. 61-244362 filed on Apr. 22, 1985).

However, such disinfector units for contact lenses are provided in a case body with an integral plug designed to be operable with one commercial power source, and cannot thus be used in countries and districts varying in commercial power source standards.

SUMMARY OF THE INVENTION

It is the first object of the present invention to provide a disinfector unit for contact lenses which is usable in various countries varying in commerical power source standards, i.e., the voltage and type of plug applied.

It is the second object of the present invention to provide a disinfector unit which does not only attain the first object but is also of small size and lightweight and so convenient to carry and store.

DETAILED DESCRIPTION

Figure 1:
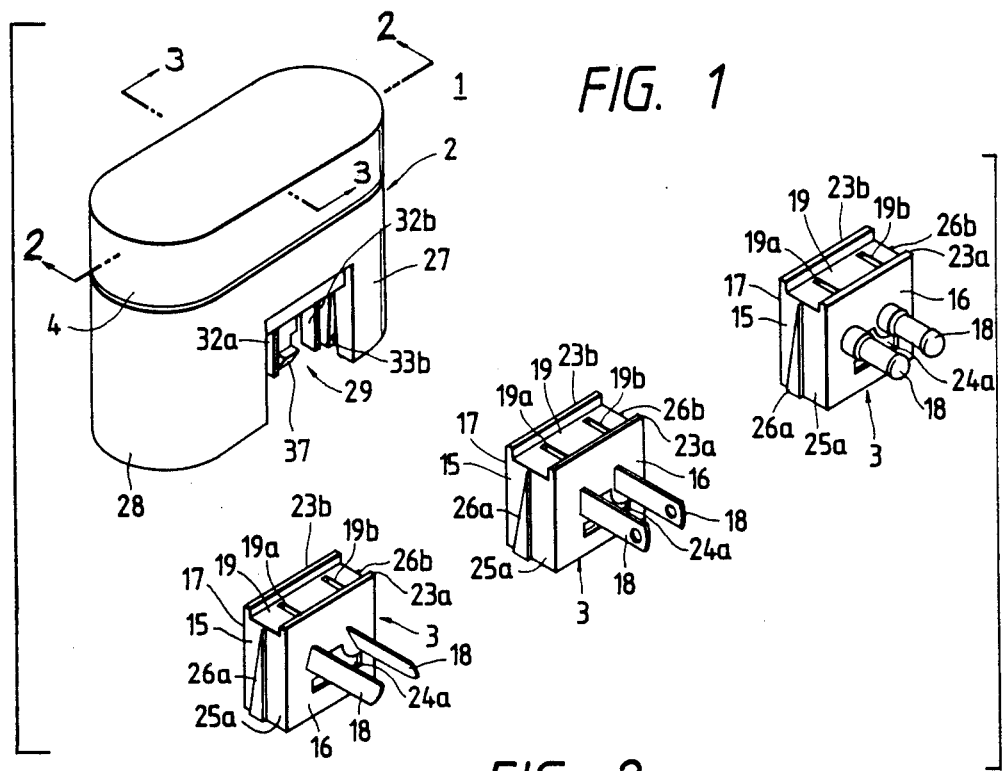
FIG. 1 is a perspective view of one embodiment of the present invention.

Referring to FIGS. 1 to 5 showing together one embodiment of the present invention, a disinfector unit 1 for contact lenses comprises a case body shown generally at 2 and a plurality of plugs, each shown generally at 3.

The case body 2 is formed of a heat-resistant hard synthetic resin into a columnar, hollow member of an oval shape in plane. The case body 2 is also provided on its upper portion with a lens case holder portion 6 including a lid member 4. Within a hollow portion 8, there is provided a heating portion 11 comprising a heat radiating metallic plate 9 and a PCT heater element 10, which is disposed along the back side of a bottom wall 7 of the lens holder 6. Below the heating portion 11, there is provided a controller 14 for making an electrical connection between a printed circuit board 13 and the heating portion 11 through a heat shielding wall 12.

Each of the plug 3 includes a plug body 15 formed of a hard synthetic resin into a hollow rectangular shape. The plug body 15 incldues an electric conductor 22, which comprises a pair of inserts 18 and 18 formed into a shape accommodative to outlets of standards varying with plugs and a pair of insert-receiving terminals 21a and 21b connected thereto. The inserts 18 and 18 extends from a front wall 16 of the plug body 15, while the insert-receiving terminals 21a and 21b are disposed within a hollow portion 20 in the plug body 15 and exposed through narrow slots 19a and 19b, each of a rectangular shape and formed in an upper wall 19. The plug 3 includes rims 23a and 23b along the upper end edges of the front and rear walls 16 and 17, and the front and rear walls 16 and 17 are provided with engaging grooves 24a and 24b in their outer central positions. Further, side walls 25a and 25b of the plug body 15 are provided with vertically extending guide ribs 26a and 26b on their outer central faces. The guide ribs 26a and 26b are upwardly tapered off.

Figure 2:
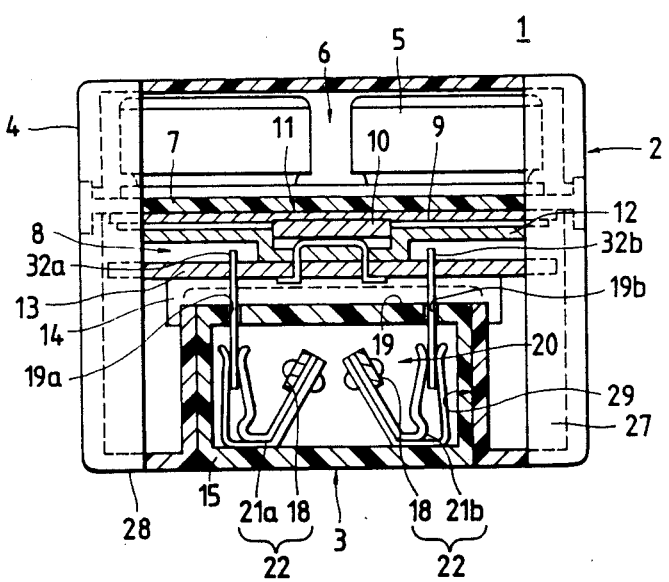
FIG. 2 is a sectional view taken along the line 2—2 of FIG. 1, in which the plug is shown fitted in the case body.
Figure 3:
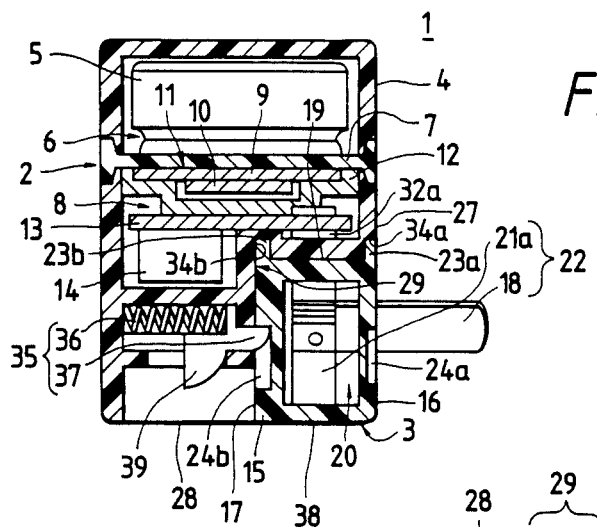
FIG. 3 is a sectional view taken along the line 3—3 of the FIG. 1, in which the plug is shown fitted in the case body with the inserts located inside.
Figure 4:
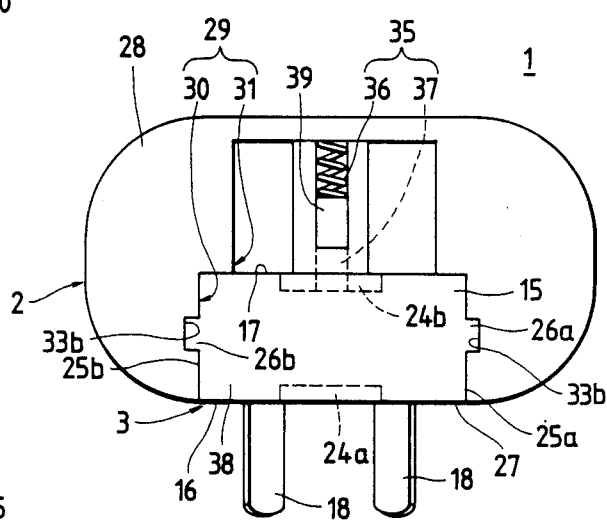
FIG. 4 is a bottom view of FIG. 1, in which the plug is shown fitted in the case body with the inserts located outside.

On the other hand, the case body 2 is provided with a cavity 29 formed by cutting out a one side wall 27 of large width and a bottom wall 28. As illustrated in FIG. 2, the cavity 29, open forward and downward, are defined by two sub-cavities 30 and 31. Fitted into the first sub-cavity 30 is the plug body 15 of the plug 3 and plugged in the second sub-cavity 31 are the inserts 18 and 18. Through the first sub-cavity 30, a pair of blade-form input terminals 32a and 32b extend downward. The input terminals 32a and 32b are supported in place at their ends fixed to the printed circuit board 13 disposed within the case body 2. When the plug 3 is fitted in the cavity 29, the input terminals 32a and 32b are inserted into the insert-receiving terminals 21a and 21b for connection with the conductor 22. Opposite side walls of the first sub-cavity are provided in their middle portions with guide grooves 33a and 33b in opposite relation. The guide grooves 33a and 33b are upwardly tapered off and open in their bottom faces, so that the guide ribs 26a and 26b formed on both side walls of the plug body 15 can be fitted thereinto from below. A top wall of the first sub-cavity 30 is provided at its front and rear end edges with a step 34a and a groove 34b, respectively. When the plug 3 is fitted in the cavity 29, the step 34a and groove 34b serve to receive the rims 23a and 23b formed at the front and rear upper ends of the plug body 15, thereby limiting the back and forth movement of the plug 3.

An engaging member 35 is vertically provided on a top wall of the second sub-cavity 31. When the plug 3 is fitted in the cavity 29, the engaging member 35 serves to fix the plug 3 to the case body 2, thereby limiting its vertical movement. The engaging member 35 includes an engaging protrusion 37 movable to and fro into the first sub-cavity 30 by being biased by a push spring. The engaging protrusion 37 comes in engagement within the engaging groove 24a or 24b, both formed on the front and rear faces of the plug body 15 of the plug 3 fitted in the cavity 29.

Reference will now be made to how to use the disinfector unit thus constructed for contact lenses.

First of all, the plug coinciding with the outlet for commerical powder available in a country or district in which the user stays is selected from a plurality of the plugs 3 including pairs of the inserts 18 and 18 meeting the standards of varying outlets for commercial power, as illustrated in FIG. 1.

Figure 5:
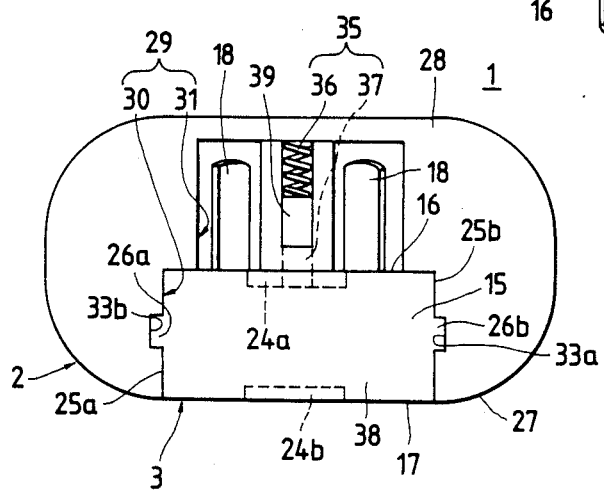
FIG. 5 is a bottom view, in which the plug is shown fitted in the case body with the inserts located inside.

Then, the thus selected plug 3 is fitted in the cavity 29, while the inserts 18 and 18 are located inside and positioned in the first sub-cavity from below the case body 2 and the plug body 15 is positioned in the second sub-cavity 31. At this time, while the guide ribs 26a and 26b are respectively fitted and inserted in the guide grooves 33a and 33a, the plug is correctly positioned so that the rims 23a and 23b engage the steps 34a and 34b with the engagement of the engaging protrusion 37 within the engaging groove 24a. The input terminals 32a and 32b projecting into the first sub-cavity 30 are inserted into the insert-receiving terminals 21a and 21b within the plug 3 for connection to each other. As illustrated in FIGS. 2 and 5, the front wall 16 and bottom wall 38 of the plug 3 are then flush with the side walls 27 and 28 of the case body 2, respectively, so that the plug 3 is completely embedded in the case body 2 and fixed there.

Usually, the disinfector unit is stored or carried in such state. In this state, the disinfector unit is very convenient to store or carry, partly because its overall size is included in the size of the case body 2 with the plugs 3 built in and partly because the plugs are tightly engaged by the case body 2 without fear of falling out. The plugs 3 also serve as a lid for the cavity 29.

For disinfection purposes, a knob 39 of the engaging member 35 is slid rearward against the biasing force of a spring 36 to disengage it from within the engaging groove 24a. Subsequent downward pulling causes the plug 3 to be pulled out of the cavity 29.

Next, the thus pulled-out plug 3 is reversed to and fro and fitted in the cavity 29 with its front back in a similar manner as mentioned above. At this time, the plug 3 is locked in place, while the plug body 15 is completely embedded in the case 2 and the inserts 18 and 18 project from the case body 2.

In this state, the lens case 5 containing a contact lens together with a liquid preservative is placed in the holder 6 with subsequent putting the lid 4 on, and the inserts 18 and 18 are plugged into the outlet, while the case body 2 is carried. Commercial current is supplied through the conductor 22 and the input terminals 32a and 32b to the controller 14 and the PTC heater element 10 to generate heat, with which the contact lens held in the lens case is disinfected by boiling at a given temperature for a given time.

Figure 6:
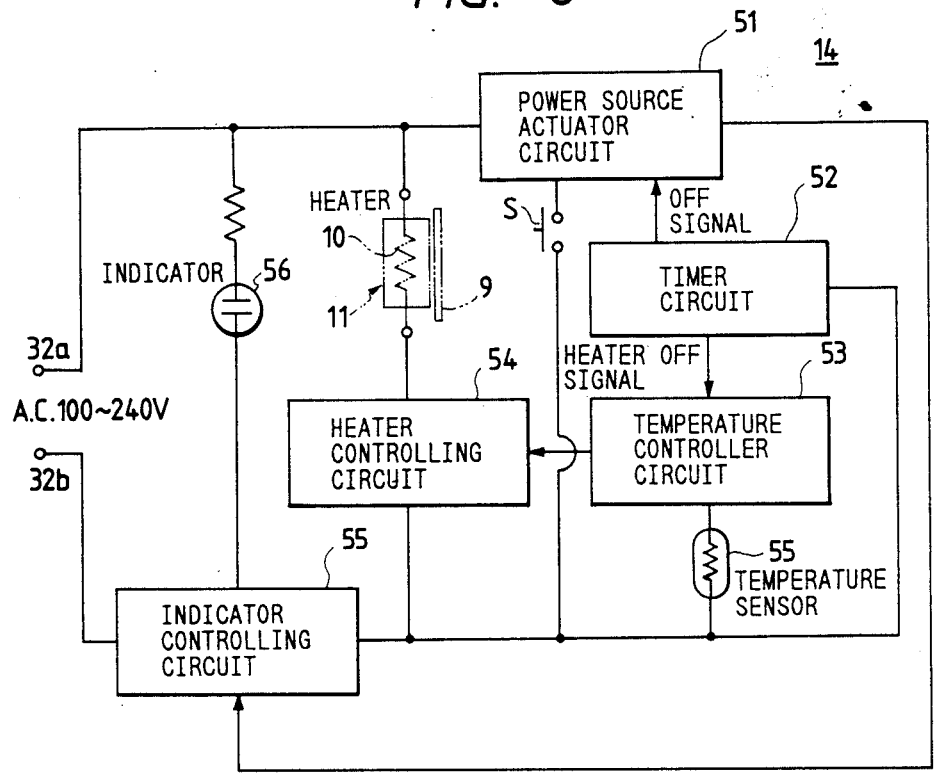
FIG. 6 is a block diagram showing the heater controller in one embodiment of the present invention.

FIG. 6 is a block diagram showing one embodiment of the electrical controller 14 capable of controlling the PTC heater element 10 corresponding to an input power of varing alternatve voltages of, say, 100 to 240 V.

The controller 14 includes a power source actuator circuit 51 having a starter switch S, a timer circuit 52 comprising, e.g., a timer integrated circuit having a transformer action operable in correspondence to an input power of an alternate voltage of 100 to 240 V, a temperature controller circuit 53, a heater controlling circuit 54 and a temperature sensor 55 comprising a thermistor, which is for instance arranged within the case body along the heating portion 11 comprising the PTC heater element 10 and the heat radiating plate 9.

In the thus constructed controller 14, an input power source is connected to the input terminals 32a and 32b. Subsequent putting the starter switch S on causes the timer circuit 52 to be actuated in response to a signal from the power source actuator circuit 51. At the same time, the temperature controller circuit 53 is actuated in response to a signal from the temperature sensor 55 to supply a given amount of current through the PTC heater element 10, thereby heating the contact lens placed in the lens case 5 to a given temperature. When the power source actuator circuit 51 is held on, an indicator controlling circuit 55 is put on to light up an indicator 56. After the lapse of a given time, i.e., the time required for disinfection, the preset timer circuit is held off. In response to an off signal from the timer circuit, the power source actuator circuit 51, the temperature controlling circuit 53 and the indicator controlling circuit 55 are then put off, so that the generation of heat by the PTC heater element 10 is brought to an end and the indicator 56 is put off and restored to the original state for the completion of disinfection.

Figure 7:
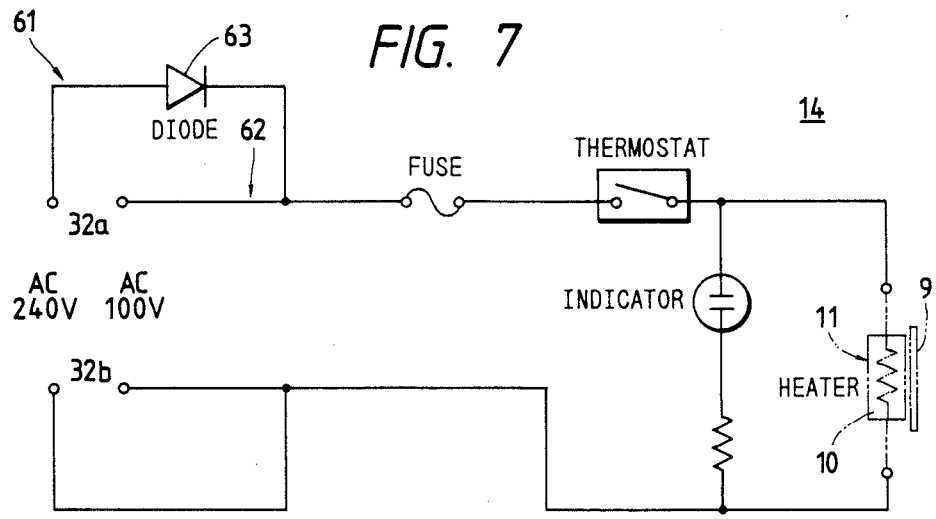
FIG. 7 is a wiring diagram showing one embodiment of the block diagram of FIG. 6.

FIG. 7 is a circuit (wiring) diagram in another controller 14. The controller 14 controls the PTC heater element 10 using a thermostat. The supply of power to the PTC heater element 10 is achieved by using two input circuits 61 and 62 corresponding to two different input voltages of, say, 100V and 240V and connecting a diode 63 to the input circuit 61 on the high-voltage side for reduction to the same voltage as the voltage of the input circuit 62 on the low-voltage side.

After the completion of the predetermined disinfection, the case body 12 is again carried to pull the inserts 18 and 18 out of the outlet. In this state where the plug 3 is firmly engaged with the case body 2, it is again unlikely that the plug 3 is separated from the case body 2.

Next, after the lens case 5 is removed as such or subsequent to taking off the lid 4, the plug 3 is pulled out of the cavity 29 in a similar manner as already mentioned. Then, the plug 3 is again reversed and fitted in the cavity with its front back for storage or carrying.

Figure 8:
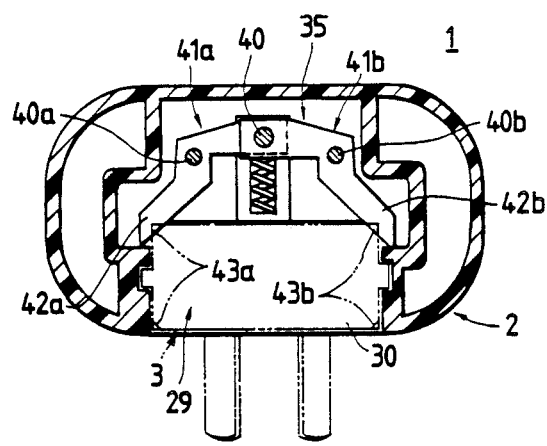
FIG. 8 is a cross-sectional view showing another embodiment of the present invention.
Figure 9:
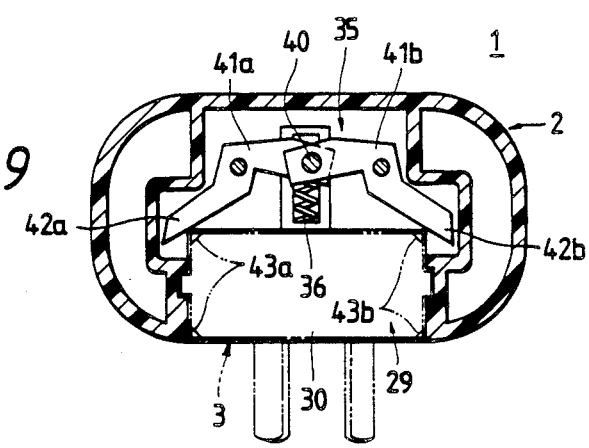
FIG. 9 is a cross-sectional view of FIG. 8, in which the engaging member is shown disengaged.
Figure 10:
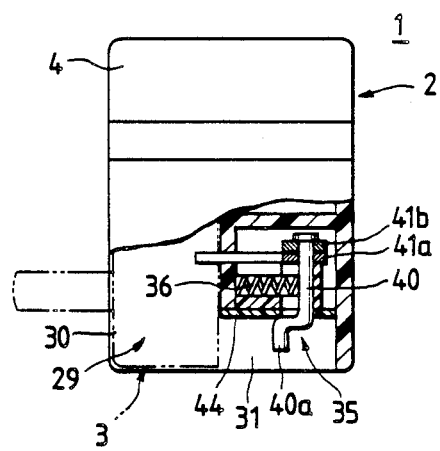
FIG. 10 is a partly cut-away side view showing the embodiment of FIG. 8.

FIGS. 8, 9 and 10 show another embodiment of the engaging member 35 for engaging the plug 3 with the case body 2.

The engaging member 35 comprises a pair of grip members 41a and 41b arranged on the case body 2 and a pair of engaging grooves formed in the plug 3. The grip members 41a and 41b are supported at their fixed ends on a shaft 40 movable toward or away from the top wall of the second sub-cavity 31 of the cavity 29 in which the inserts 18 and 18 of the plug 3 are fitted and urged by the push spring 36 toward the first sub-cavity 30 in which the plug body 15 of the plug 3 is fitted, and the fixed ends are supported on shaft portions 40a and 40b so that extreme engaging portions 42a and 42b are opened or closed by the movement of the movable shaft 40. When the engaging portions 42a and 42b are closed, they engage within engaging grooves 43a and 43b formed in the plug fitted in the cavity 29.

According to such an arrangement, the plug 3 can be firmly held in place, since it is gripped and engaged on its both sides by force of the push spring 36. In addition, the disinfector unit can be improved in terms of its appearance, since the the grip members 41a and 41b can be covered with a cover 44 while only the knob 40a for operating the movable shaft 40 is permitted to be exposed in the second sub-cavity 31.

What is claimed is

1. A disinfector unit for contact lenses comprising in combination:
   a hollow case body including a lidded lens case holder disposed thereabove, a heating portion disposed therein, a controller for receiving a power of varying voltage to hold said heating portion at a predetermined temperature for a predetermined time and a cavity formed in one side thereof, into which input terminals connected to said controller extend; and
   a plurality of plugs, each including an electric conductor from which extended are inserts corresponding to outlets of varying standards,
   each of said plug being capable of being fitted in said cavity in said case body from the side on which said inserts are provided or the opposite side, so that when it is fitted in said cavity from the side on which said inserts are provided (with said inserts located inside), it is completely embedded in said case body while when it is fitted in said cavity from the opposite side (with said inserts located outside), said inserts are extended from said case body and said conductor is connected to said input terminals.

2. A disinfector unit for contact lenses as claimed in claim 1, wherein said case body includes a movable shaft movable toward or away from a top wall of a second sub-cavity of said cavity in which said inserts of said plug are to be fitted and a pair of grip members supported at their fixed ends on said movable shaft and including engaging members formed at the other ends, said engaging members being closed or opened by the movement of said movable shaft, and
   said plug includes a plug body provided in its longitudinal ribs with engaging grooves within which said engaging members are to engage.

3. A disinfector unit for contact lenses as claimed in claim 1, wherein said cavity in the said case body is open at its front and bottom walls.

4. A disinfector unit for contact lenses as claimed in claim 3, wherein said cavity in said case body includes vertically extending guide grooves in the outer central faces of its both side walls, which are upwardly tapered off and open on its bottom face, and
   said plug includes guides on its both side walls, said guides being to engage within said guide grooves.

5. A disinfector unit for contact lenses as claimed in claim 3, wherein said case body includes a cavity defined by a first sub-cavity located outside for receiving said plug body and a second sub-cavity located inside for receiving said inserts, said first sub-cavity having a step and groove at the front and rear end edges of its top wall and said second sub-cavity having an engaging member, and
   said plug including at its front and rear upper ends ribs to engage said step and said groove and in its front and rear faces engaging grooves to engage said engaging member.

* * * * *